United States Patent [19]
Burrell et al.

[11] Patent Number: 5,306,707
[45] Date of Patent: Apr. 26, 1994

[54] PERFUMED PRODUCTS

[75] Inventors: John W. Burrell, Ashford; Stuart B. Fraser, Little Neston; Neil Kilcullen, Moreton; Alexander Martin, Helsby; James B. Melville, Eastham, all of Great Britain

[73] Assignee: Unilever Patent Holdings B.V., Rotterdam, Netherlands

[21] Appl. No.: 13,196

[22] Filed: Jan. 29, 1993

Related U.S. Application Data

[63] Continuation of Ser. No. 671,618, Mar. 20, 1991, abandoned.

[30] Foreign Application Priority Data

Mar. 20, 1990 [GB] United Kingdom ............. 9006254.8

[51] Int. Cl.$^5$ .............................................. A61K 7/46
[52] U.S. Cl. ....................................................... 512/2
[58] Field of Search ........................................... 512/2

[56] References Cited

U.S. PATENT DOCUMENTS

| | | | |
|---|---|---|---|
| 3,767,787 | 10/1973 | Segal | 512/2 |
| 4,778,783 | 10/1988 | Gondra et al. | 512/2 |
| 4,966,754 | 10/1990 | Purohit et al. | 424/195.1 |

FOREIGN PATENT DOCUMENTS

| | | | |
|---|---|---|---|
| 0144417 | 8/1988 | European Pat. Off. | A61K 31/235 |
| 3910652 | 10/1990 | Fed. Rep. of Germany | A61K 7/50 |
| WO84/04886 | 12/1984 | PCT Int'l Appl. | A61K 31/235 |

OTHER PUBLICATIONS

Kawasaki, Chem. Abst., vol. 103, #109, 8165 (1985).
Kabra, Chem. Abst., vol. 102, #225817w (1985).
Yanagi et al, Fragrance Journal, 1989(2), pp. 14–23.
Morris et al, Journal of the American Oil Chemists' Society, vol. 56, pp. 595–603 (1979).
Blakeway, Seifen-ole-Fette-Wachse, vol. 116, No. 9, pp. 357–359 (Jun. 13, 1990).
Dean et al, Int. J. of Food Microbiology, vol. 5, pp. 165–180 (1987).
Blakeway, S.P.C., pp. 201–203 (Apr., 1986).
Munzing et al., J. Soc. Cosmetic Chemists, vol. 23, pp. 841–852 (1972).
Kabara, Cosmet. Sci. Technol. Ser., vol. I, pp. 237–273 (1984).
Isacoff, The Chemistry and Manufacture of Cosmetics, vol. III, 2nd Ed., pp. 85–109 (1975).
Blakeway et al, J. Am. Oil. Chem. Soc., vol. 56, pp. 595–603 (1979).
Strum, S.P.C., pp. 475–478 (1979).
Leak, et al, "Challenge tests and their predictive ability", pp. 129–146.

Primary Examiner—James H. Reamer
Attorney, Agent, or Firm—Cushman, Darby & Cushman

[57] ABSTRACT

The invention concerns perfuming and protecting against microbial spoilage products, which are not intended for human or animal ingestion and which comprise at least 25% of water and 0–60% of a surface active material, by incorporating therein a preservative perfume. Preservative perfumes consist for at least 30% by weight of perfume ingredients which need at least 3 inoculations for failure in the individual challenge test. Preferred effective perfumes themselves need at least 5 inoculations for failure in the perfume challenge test.

16 Claims, No Drawings

PERFUMED PRODUCTS

This is a continuation of application Ser. No. 07/671,618, filed on Mar. 20, 1991, which was abandoned upon the filing hereof.

The invention concerns products which are not intended for human or animal ingestion and which normally contain a perfume to provide them with an agreeable odor. More specifically the invention concerns products containing a preservative perfume which not only serves to provide an agreeable odor, but also counteracts microbial spoilage of the product. The invention also concerns preservative perfumes useful for this purpose.

Microbial spoilage is a well known problem with many perfumed products. It is caused by microbial contamination either during production, or, more importantly, when in use by the consumer. Conventionally this problem has been solved by the addition of well known preservatives such as: formaldehyde, 2-bromo-2-nitro-propanediol, para-hydroxybenzoic acid esters (parabens), sorbic acid and potassium sorbate, benzoic acid and sodium benzoate, diazolidinyl urea, dimethylol dimethyl hydantoin, imidazolidinyl urea, 1,2-benzisothiazolin-3-one. However, doubts have been expressed recently as to the innocuousness of such compounds to human health. Thus, the need has arisen to restrict their use as much as possible.

Many conventional perfume ingredients, essential oils as well as single perfume chemicals, have been tested for antimicrobial properties against many different microorganisms with variable results. Thus, S. G. Dean and G. Ritchie, Int. Journ. of Food Microbiology. 5 (1987), 165-180 examined 50 essential oils for their antibacterial properties against 25 genera of bacteria using an agar diffusion technique and determining zones of inhibition. They concluded that gram-positive as well as gram-negative bacteria were susceptible to (some of the) essential oils. J. Blakeway, S.P.C. April 1986, 201-203 determined the antimicrobial activity of 50 essential oils against 22 micro-organisms (bacteria, yeasts and fungi) also measuring zones of inhibition. His conclusion was that essential oils have generally little activity against gram-negative bacteria. Angelica for instance, which was found to be active against all 25 bacteria including *Escherichia coli, Serratia marcescens* and *Pseudomonas aeruginosa,* by Dean and Ritchie, is decribed as inactive against these bacteria by Blakeway. J. A. Morris et al, J. Am. Oil Chem. Soc. 56 (1979), 595-603 tested 521 perfume ingredients, including essential oils and single perfume chemicals, against *Staphylococcus aureus, Escherichia coli* and *Candida albicans* and 212 of these also against a Corynebacterium sp. They measured zones of inhibition and the positive ingredients were subjected to a minimum inhibitory concentration test in a liquid culture. 44% of the 521 were inhibitory against at least 1 micro-organism and 12% against all three. H. P. Münzing and H. Schels, J. Soc. Cosmetic Chemists 23 (1972), 841-852 measured the activity of 37 perfume ingredients of natural and synthetic origin in a liquid culture against *Staphylococcus aureus, Escherichia coli, Proteus vulgaris* and *Pseudomonas aeruginosa.* They again found that the gram positive *S. aureus* was more affected than the gram-negative bacteria. Furthermore they found random activity of the separate ingredients against the different microorganisms, which means that it seems to be impossible to predict the activity of a specific perfume ingredient against one micro-organism on the basis of its activity against another micro-organism. From their results they were able to prepare simple perfume compositions which in liquid culture inhibited growth of three bacteria, but not of *Ps. aeruginosa.* One composition was moderately active against these three bacteria when added in 0.2% to an O/W emulsion. H. Isacoff in "The Chemistry and Manufacture of Cosmetics", Chapter 8, (Ed. M. G. de Navarre), Vol. III, 2nd Edition, Orlando 1975, reviewed the existing literature on preservation with essential oils and perfume compounds and based on this information prepared two perfume compositions which were tested as preservatives in O/W emulsions against *Staphylococcus aureus, Pseudomonas aeruginosa, Bacillus subtilis, Aspergillus niger* and *Candida albicans,* with mixed success. A further review of the literature was prepared by J. J. Kabara, "Aroma Preservatives" in "Cosmet. Sci. Technol. Ser, Vol 1 (Cosmet. Drug Preserv. 1984)." 237-273. He did not cite any further examples of actual perfume compositions which were tested, either as such or after application in a product, for their antimicrobial activity. W. Sturm, S.P.C. 1979, 475-478 described the repeated use of well known but unspecified perfume ingredients to inhibit or reduce the growth of equally unspecified skin bacteria. In EP-B-144417 the use of mixtures of cinnamaldehyde and parabens as preservatives is described. U.S. Pat. No. 4,590,215 describes the use of alphacadinol as a bactericide against Streptococcus mutans. Thus, reviewing the extensive literature available on the subject of antimicrobial activity of perfume ingredients, the following conclusions may be drawn:

a) Conflicting results have been obtained for one and the same ingredient against one and the same micro-organism.

b) Results against one micro-organism cannot be translated to another micro-organism.

c) Results have primarily been obtained as zones of inhibition in agar diffusion techniques and many compounds may look promising under these circumstances; phenolic type compounds are well known examples. However, this test method does not reflect actual in use conditions in products to be preserved.

d) Very few perfume compositions have been tested for their antimicrobial activity and with limited success.

e) The micro-organisms against which the perfume ingredients have been tested are mostly skin related species and not those which are primarily responsible for microbial spoilage of products.

In spite of various suggestions in the literature cited above that perfume ingredients to be used in the preparation of a perfume for a product may be chosen not only for their olfactive contribution but also for their preservative effect, no product appears to be known which is effectively protected against microbial spoilage by the perfume incorporated therein.

It has now been found that products may be protected against microbial spoilage by incorporating therein a preservative perfume comprising perfume ingredients which require a certain minimum "number of inoculations to failure" in the individual challenge test as hereinafter described.

The effectiveness of the protection depends on the antimicrobial effectiveness of the perfume ingredients as determined by the individual challenge test, and on the total quantity of effective ingredients in the perfume. The individual challenge test allows a much more accurate prediction of actual effectiveness in a perfumed product than the methods used for testing perfume ingredients in the prior art. By varying the parameters given above a preservative perfume may be composed which can replace conventional preservatives to any desired extent. Additionally, preservative perfumes tend to be more effective, the more different effective ingredients are present in them.

Generally, it will be desirable to limit the use of conventional preservatives as much as possible, usefully to below 0.01% or even 0.001% by weight of the product. Preferably a preservative perfume will be used which completely obviates the use of conventional preservatives. Products containing such perfumes may be free of conventional preservatives.

The effectiveness of the preservative perfumes of the invention may vary with the composition of the actual product to be preserved as is also well known for conventional preservatives, compare e.g. Mitsuo Yanaki and Yoichi Shimatani, Fragrance Journal, 1989 (2), pp. 14-23. The exact amount needed to obtain satisfactory preservative action may be easily established with the perfume challenge test as herinafter described using the actual product to be preserved as the test medium. Generally, products still containing small quantities of conventional preservatives as described above will need at least 0.05% w/w of preservative perfume for satisfactory preservation; 0.1% (w/w) or more of preservative perfume should preferably be present in products which are substantially free of conventional preservatives.

Antimicrobially effective perfume ingredients are those which need at least 3 inoculations to failure in the individual challenge test. Such perfume ingredients are hereinafter called "effective ingredients". Preferably effective ingredients are used which need at least 5 inoculations to failure in the individual challenge test. Particularly effective ingredients are found among compounds according to the formula:

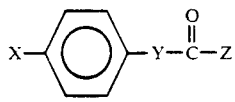

wherein X denotes a hydrogen atom, a methyl or a methoxy group, Y denotes an alkylene, alkenylene, alkyleneoxy or alkenyleneoxy group or may be absent and Z denotes a hydrogen atom or a hydroxy, alkyl or alkoxy group, provided that when Z is a hydroxy or alkoxy group and Y is an alkylenoxy or alkenylenoxy group the oxygen atom in Y is attached to the phenyl-group, provided further that when Y is absent Z does not denote a hydroxy group, and wherein Y and Z together have no more than 4 carbon atoms, or the formula:

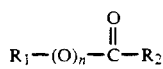

wherein $R_1$ denotes a saturated or unsaturated aliphatic group, n is 0 or 1, $R_2$ denotes a hydrogen atom or an alkyl group of up to 5 carbon atoms and wherein $R_1$ and $R_2$ together have no more than 14 carbon atoms.

Preservative perfumes according to the invention consist of at least 30% by weight, preferably at least 40%, more preferably more than 50 % or even 60% by weight of effective ingredients. Moreover, the number of different effective ingredients in such a perfume should preferably be 2 or more, more preferably 4 or more. The remainder of the perfume may consist of perfume ingredients chosen only for their olfactory contribution to the perfume. The effectiveness of a preservative perfume may be tested in the perfume challenge test as hereinafter described. "Effective" perfumes are defined as preservative perfumes which need at least 3 inoculations to failure. Preferred effective perfumes need 5 or more inoculations to failure. Particularly effective perfumes are those which need 20 or more inoculations.

Products to be preserved according to the invention are those which are not intended for human or animal ingestion and which would be susceptible to microbial spoilage under normal production or use conditions. Included in this definition for purposes of the present invention are products for dental care, which although not intended for ingestion may nevertheless accidentally enter the gastro-intestinal tract.

Products to be preserved will contain a certain quantity of water, generally at least 25% by weight, in most cases 30% or more. Furthermore, such products will usually contain some surface active material, either as an emulsifier, if the product is an emulsion, or as a detergent active material if the product has some kind of cleaning activity. Generally, the concentration of surface active material in the product will be 0-60% w/w; at higher concentrations of surface active material a preservative is hardly ever needed because microbial spoilage is unlikely to occur. Usually the level of surface active material will be 50% w/w or lower. On the other hand, the level of surface active material will usually be at least 0.1% w/w. Examples of products containing emulsifiers are: hand and body lotions, skin creams, sunscreen agents, hair conditioners, water-based adhesives and water-based paints. Examples of products containing detergents are: shampoos, dishwashing liquids, heavy duty cleaners, general purpose cleaners, liquid abrasive cleaners, liquid soaps, fabric softeners. Some products may fall into both categories. Other components which may be present in products preserved according to the invention are: colorants, antioxidants, structuring agents, pH buffers, abrasive particles, builders, UV absorbers, foam boosters, etc. As outlined above, the effectiveness of a preservative perfume in a given product is also influenced by the physico-chemical characteristics of that product and thus by the other components present in the product. However, since the test environment used in the challenge tests as hereinafter described generally reflects the conditions prevalent in most perfumed products, preservative perfumes as hereinbefore defined will give satisfactory results in a wide variety of products.

Typical quantities of water and surface active material in different kinds of product are tabulated below:

| Product | Surf. act. material (%) | Water (%) |
| --- | --- | --- |
| Oil-in-water cream | 10 | 60 |
| Water-in-oil cream | 2 | 60 |
| Liquid abrasive cleaner | 12 | 32 |
| General purpose cleaner | 8 | 90 |
| Shampoo | 20 | 75 |
| Window cleaner | 0.2 | 90 |
| Fabric softener | 5 | 94 |

| Product | Surf. act. material (%) | Water (%) |
|---|---|---|
| Hair conditioner | 5 | 90 |
| Dishwashing liquid | 40 | 55 |
| Heavy duty cleaner | 10 | 55 |

The individual challenge test is carried out as described below:

100 g of a solution containing 2% iso-octyl-phenoxypolyethoxy-ethanol, 0.5% sodium dodecyl sulphate and 97.5% distilled water is aseptically weighed into a sterile conical flask. The perfume ingredient to be tested is then mixed into the solution at a concentration of 3 mmoles per 100 g. A 1 ml sample of this solution is removed and set aside for a total viability count (TVC). The solution is then inoculated with 1 ml of a mixed culture of *Pseudomonas cepacia* and *Enterobacter cloacae* containing about $10^9$ organisms and incubated at 28° C. overnight. A 1 ml sample is removed and added to 9 ml of an aqueous solution of 0.1% peptone and 2% Tween 80. The resulting sample solution is then diluted ten-fold and a 1 ml aliquot therefrom and from the undiluted sample solution is placed onto 2 separate sterile petri plates. These aliquots are then mixed with tryptone soya agar and incubated at 28° C. for 48 hours. A new 1 ml inoculum is added to the 100 g test solution and the procedure is repeated until the solution has failed the challenge test. The solution is considered to have failed the challenge test when there is a TVC of greater than 100 colonies for each plate for two consecutive samples. The number of inoculations before the first of these two samples was drawn is counted as the "number of inoculations to failure".

The perfume challenge test is carried according to the same procedure, however the 100 g test solution is caused to contain a concentration of 0.4% (w/w) of the complete perfume instead of 3 mmoles of perfume ingredient.

Effective ingredients needing 5 or more inoculations to failure in the individual challenge test are e.g.:
phenylethyl formate
trans-2-hexenal
cis-3-hexenyl acetate
phenylacetaldehyde
cinnamic aldehyde
phenylacetic acid
cinnamic acid
benzyl formate
prenyl acetate
2-methyl-2-hepten-6-one.

Effective ingredients needing from 3 to 5 inoculations to failure in the individual challenge test are e.g.:
methyl hexyl ketone
methyl amyl ketone
amyl propionate
amyl acetate
methyl benzoate.

COMPARATIVE EXAMPLES I, II AND III

The perfume recipes below were published by Münzing and Schels and by Isacoff (vide supra) and according to these publications exhibited antimicrobial activity in o/w emulsions:

| | I | II | III |
|---|---|---|---|
| Geraniol | 40 | 25 | 20 |
| Nerol | 10 | 5 | 5 |
| Citronellol | 10 | 15 | 1 |
| Rhodinol | 10 | 0 | 5 |
| Geranium Bourbon | 0 | 1 | 0 |
| Linalool | 9 | 3 | 5 |
| Palmarosa oil | 0 | 2 | 0 |
| Eugenol | 1.5 | 1 | 1 |
| Rosewood oil | 0 | 8 | 0 |
| Hydroxycitronellal | 0 | 10 | 0 |
| Nonal (10%) | 0 | 1 | 0 |
| Octanal (10%) | 0 | 1 | 0 |
| Citral | 0 | 1 | 0 |
| Guaiacwood oil | 0 | 2 | 0 |
| Lavender oil | 0 | 12 | 0 |
| Lavender spike Spanish | 0 | 2 | 0 |
| Cinnamic aldehyde | 1 | 1 | 0.5 |
| Rhodinol coeur | 0 | 10 | 0 |
| Phenylethyl alcohol | 15.5 | 0 | 60 |
| Benzyl acetate | 3 | 0 | 2.5 |
| | 100 | 100 | 100 |

Perfumes prepared according to these recipes were subjected to the perfume challenge test above Perfume I failed after 1 inoculation, Perfumes II and III after 2 inoculations. Thus, neither of these perfumes fulfilled the minimum test criterion for effective preservative perfumes mentioned above.

EXAMPLES 1-5

Preservative perfumes were prepared according to the following recipes:

| | 1 | 2 | 3 | 4 | 5 |
|---|---|---|---|---|---|
| Phenylacetic acid* | 2 | 2 | 2 | 2 | 2 |
| Cinnamic acid* | 5 | 5 | 5 | 5 | 5 |
| Phenylacetaldehyde* | 4 | 4 | 4 | 3 | 3 |
| 2-Methyl-2-hepten-6-one* | 3 | 3 | 3 | 5 | 5 |
| Phenylethyl formate* | 10 | 10 | 10 | 15 | 15 |
| cis-3-Hexenyl acetate* | 2 | 2 | 2 | 1 | 1 |
| Prenyl acetate* | 1 | 1 | 1 | 1 | 1 |
| Benzyl formate* | 11 | 11 | 11 | 7 | 7 |
| Cinnamic aldehyde* | 2 | 2 | 2 | 1 | 1 |
| Linalool | 10 | 10 | 4 | 4 | 8 |
| 2-Phenylethanol | 15 | 10 | 9 | 8 | — |
| Hexyl-cinnamic aldehyde | — | 5 | 5 | — | 5 |
| Geraniol | 8 | 4 | 6 | — | — |
| Geranyl acetate | 2 | 1 | 2 | — | — |
| Citronellol | 8 | 4 | 12 | 5 | 5 |
| Citronellyl acetate | 2 | 1 | 6 | — | — |
| Hydroxycitronellal | — | 2 | — | 5 | 28 |
| Lilial | — | 3 | — | — | — |
| Methyl dihydrojasmonate | 5 | 5 | — | — | — |
| Galaxolide[1] | 5 | 5 | 8 | 5 | — |
| Tonalid[2] | — | — | 2 | — | — |
| Linalyl acetate | 3 | 10 | 6 | — | — |
| Chandanol[3] | 2 | — | — | — | — |
| Terpineol | — | — | — | 6 | 4 |
| Heliotropin | — | — | — | 13 | 5 |
| Cinnamic alcohol | — | — | — | 9 | — |
| Iso-Methyl-ionone (alpha) | — | — | — | — | 5 |
| Lixetone[4] | — | — | — | 5 | — |
| | 100 | 100 | 100 | 100 | 100 |

*effective ingredients
[1] to [4] trademarks of various perfume houses.

The perfumes were subjected to the perfume challenge test. They all needed more than 5 inoculations to failure in the perfume challenge test. Example perfumes 1 and 4 even needed more than 30 inoculations.

EXAMPLE 6

A shampoo was prepared according to the following recipe:

|  | % w/w |
| --- | --- |
| Sodium laurether sulphate (2EO) | 16 |
| Alkylbetaine | 2 |
| Coconut diethanolamide | 1 |
| Sodium chloride | 0.1 |
| Preservative perfume according to Example 4 | 0.4 |
| Water | 80.5 |

This shampoo remained stable against microbial spoilage under normal use conditions.

COMPARATIVE EXAMPLES IV AND V

Perfumes were prepared according to the recipes below. The first 19 components together making up at least 56% w/w of the perfumes were chosen from those found most antimicrobially active by J. A. Morris et al, referred to above.

|  | IV | V |
| --- | --- | --- |
| Oakmoss absolute 570 | 2 | 2 |
| Ethyl linalool | 2 | 8 |
| Geraniol | 12 | 16 |
| Citronellol | 10 | 16 |
| Citral | 2 | 3 |
| Lemongrass (Guatemalan 75%) | 2 | 1 |
| Eugenol | 2 | 1.6 |
| Iso-eugenol | 2 | 0.4 |
| Anethol | 2 | 0.4 |
| Fennel (bitter) | 2 | 0.4 |
| Clove leaf oil | 2 | 0.8 |
| Cinnamon leaf oil | 2 | 0.8 |
| Thyme (white) | 2 | 0.4 |
| Pimento berry | 2 | 0.8 |
| Basil oil | 2 | 0.4 |
| Phenylpropyl aldehyde | 2 | 1 |
| Phenylacetaldehyde (50%) | 2 | 0.8 |
| Helional* | 2 | 2 |
| Isopropyl quinolene | 2 | 0.8 |
| Actives according to Morris: | 56 | 56.6 |
| Geranyl acetate | 2 | 2 |
| Citronellyl acetate | 2 | 2 |
| Methyl dihydrojasmonate | 5 | 5 |
| Galaxolide* | 5 | 5 |
| Linalyl acetate | 3 | 3 |
| Chandanol* | 2 | 2 |
| Linalool | 10 | 10 |
| Phenylethanol | 15 | 15 |
|  | 100 | 100.6 |

*trademarks of various perfume houses

The perfumes were subjected to the perfume challenge test and both failed after 1 inoculation.

EXAMPLE 7

A shampoo was prepared according to the following recipe:

|  | % w/w |
| --- | --- |
| Sodium laurether sulphate (2EO) | 16 |
| Lauryl betaine | 2 |
| Coconut diethanolamide | 1 |
| Sodium chloride | 1.5 |
| Water | 79.5 |

The perfumes of examples 1-5, and comparative examples IV and V were all subjected to the perfume challenge test, however using the above shampoo formulation as the test medium. The perfumes were tested in a concentration of 0.4% w/w in the test medium and some also in concentrations of 0.6 and 1.0%. The number of inoculations to failure are tabulated below:

|  | Perfume examples | | | | | | |
| --- | --- | --- | --- | --- | --- | --- | --- |
| % perfume | 1 | 2 | 3 | 4 | 5 | IV | V |
| 0.4 | 29 | 29 | 33 | 30 | 30 | 1 | 1 |
| 0.6 | >40 |  |  | >40 |  | 1 | 1 |
| 1.0 | >40 |  |  | >40 |  | 1 | 1 |

From the results it is apparent that the perfumes of comparative examples IV and V, although consisting for more than 50% of components which are described in the prior art as antimicrobially effective, do not have a reasonable preservative action even at a concentration of 1.0% in the shampoo, whereas the perfumes according to the invention effectively preserved the shampoo at a concentration of 0.4%.

EXAMPLE 8

A skin lotion was prepared according to the following recipe:

|  | % w/w |
| --- | --- |
| Stearic acid | 1.0 |
| Light mineral oil | 3.0 |
| Cetyl alcohol | 0.3 |
| Glycerol monostearate | 0.6 |
| Triethanolamine | 0.5 |
| Glycerol | 2.0 |
| Carbopol 940 | 0.1 |
| Water | 92.5 |

The perfumes of examples 1 and 4 were subjected to the perfume challenge test when added in a concentration of 0.6% w/w to the above skin lotion as the test medium. Both needed 16 inoculations to failure.

We claim:

1. In a perfumed product which is subject to microbial spoilage and which comprises at least 25% of water and 0.1-60% of a surface active material, the improvement wherein said product contains less than 0.1% of conventional preservatives and 0.05% by weight or more of a preservative perfume wherein at least 30% by weight of said perfume consists of at least one antimicrobially effective perfume ingredient requiring at least three microbial inoculations to failure in an individual challenge test such that said perfume product also requires at least three inoculations to failure in the perfume challenge test, wherein said effective ingredient is selected from the group consisting of compounds according to the formula:

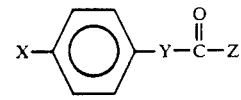

wherein X denotes a hydrogen atom, a methyl or a methoxy group, Y denotes an alkylene, alkenylene, alkyleneoxy or alkenyleneoxy group or may be absent and Z denotes a hydrogen atom or a hydroxy, alkyl or alkoxy group, provided that when Z is a hydroxy or alkoxy group and Y is an alkylenoxy or alkenylenoxy group the oxygen atom in Y is attached to the phenyl-group, provided further that when Y is absent Z does not denote a hydroxy group, and wherein Y and Z together have no more than 4 carbon atoms, or the formula:

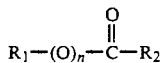

wherein $R_1$ denotes a saturated or unsaturated aliphatic group, n is 0 or 1, $R_2$ denotes a hydrogen atom or an alkyl group of up to 5 carbon atoms and wherein $R_1$ and $R_2$ together have no more than 14 carbon atoms.

2. Perfumed product according to claim 1 wherein it is substantially free of conventional preservatives and contains at least 0.1% of a preservative perfume.

3. Perfumed product according to claim 1 wherein the preservative perfume contains at least 2 different effective ingredients.

4. Perfumed product according to claim 3 wherein the preservative perfume contains at least 4 different effective ingredients.

5. Perfumed product according to claim 1 wherein the preservative perfume comprises at least 40% by weight of effective ingredients.

6. Perfumed product according to claim 1 wherein the preservative perfume needs at least 5 inoculations to failure.

7. Perfumed product according to claim 1 comprising at least 30% of water and between 0.1 and 50% of surface active material.

8. In a preservative perfume comprising conventional perfume ingredients, the improvement which comprises including therein at least 30% by weight of said perfume consists of at least one antimicrobially effective perfume ingredient requiring at least three microbial inoculations to failure in an individual challenge test such that said preservative perfume also requires at least three inoculations to failure in the perfume challenge test, wherein said effective ingredient is selected from the group consisting of compounds according to the formula:

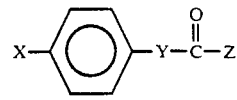

wherein X denotes a hydrogen atom, a methyl or a methoxy group, Y denotes an alkylene, alkenylene, alkyleneoxy or alkenyleneoxy group or may be absent and Z denotes a hydrogen atom or a hydroxy, alkyl or alkoxys group, provided that when Z is a hydroxy or alkoxy group and is an alkylenoxy or alkenylenoxy group the oxygen atom in Y is attached to the phenyl-group, provided further that when Y is absent Z does not denote a hydroxy group, and wherein Y and Z together have no more than 4 carbon atoms, or the formula:

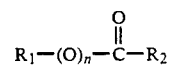

wherein $R_1$ denotes a saturated or unsaturated aliphatic group, n is 0 or 1, $R_2$ denotes a hydrogen atom or an alkyl group of up to 5 carbon atoms and wherein $R_1$ and $R_2$ together have no more than 14 carbon atoms.

9. Preservative perfume according to claim 8 containing at least 2 different effective ingredients.

10. Preservative perfume according to claim 9 containing at least 4 different effective ingredients.

11. Preservative perfume according to claim 8 containing at least 40% by weight of effective ingredients.

12. Preservative perfume according to claim 8 requiring at least 5 inoculations to failure.

13. A perfumed product according to claim 1 wherein said product is an oil-in-water cream, a water-in-oil cream, a liquid abrasive cleaner, a general purpose cleaner, a shampoo, a window cleaner, a fabric softener, hair conditioner, dishwashing liquid or heavy duty cleaner.

14. A perfumed product according to claim 13 wherein the effective ingredient is phenylacetic acid, cinnamic acid, phenylacetaldehyde, 2-methyl-2-hepten-6-one, phenylethyl formate, cis-3-hexenyl acetate, prenyl acetate, benzyl formate or cinnamic aldehyde.

15. A perfumed product according to claim 14, said product being a shampoo or skin lotion.

16. A preservative perfume according to claim 8 including at leas t one perfume component selected only for its olfactive contribution and a mixture of four or more essential ingredients constituting a total of at least 30% by weight of the perfume.

* * * * *

UNITED STATES PATENT AND TRADEMARK OFFICE
CERTIFICATE OF CORRECTION

PATENT NO. : 5,306,707
DATED : April 26, 1994
INVENTOR(S) : BURRELL et al.

It is certified that error appears in the above-indentified patent and that said Letters Patent is hereby corrected as shown below:

Claim 8, column 10, line 12, following "alkoxy group and" insert --Y--.

Claim 1, column 8, line 51, following "said perfume" delete --product--.

Claim 16, column 10, line 51, change "essential" to --effective--.

Signed and Sealed this

Ninth Day of May, 1995

Attest:

BRUCE LEHMAN

Attesting Officer        Commissioner of Patents and Trademarks